United States Patent [19]

Erhan

[11] Patent Number: 4,845,278

[45] Date of Patent: Jul. 4, 1989

[54] CROSSLINKABLE ARAMIDS

[76] Inventor: Semih Erhan, 2301 Cherry St., Apt. 12B, Philadelphia, Pa. 19103

[21] Appl. No.: 92,610

[22] Filed: Sep. 3, 1987

[51] Int. Cl.$^4$ .......................................... C07C 101/50
[52] U.S. Cl. .................... 562/435; 528/310; 528/335; 528/312; 528/350; 525/420; 562/430; 562/432; 562/44; 562/58
[58] Field of Search ........................................ 562/435

[56] References Cited

U.S. PATENT DOCUMENTS

| | | | |
|---|---|---|---|
| 3,950,380 | 4/1976 | Feit et al. | 560/12 |
| 4,036,838 | 7/1977 | Vogel et al. | 562/435 |

FOREIGN PATENT DOCUMENTS 988806  1/1983  U.S.S.R. ............................. 562/435

OTHER PUBLICATIONS

Dokunikhim et al., Chem. Abst., vol. 88, #169993d (1978).

Primary Examiner—James H. Reamer
Attorney, Agent, or Firm—Steele, Gould & Fried

[57] ABSTRACT

A new class of polymers and processes used in their preparation are described. These polymers are comprised of crosslinkable aramids, especially aramids that are based on synthetic aromatic amino acids. The aromatic amino acids suggested for this application are selected from the classes of amino benzoic acids, aminodiphenyl carboxylic acids, aminodiphenyl ether carboxylic acids, aminodiphenyl sulfide carboxylic acids, amino diphenyl sulfoxide—and sulfone carboxylic acids, aminonaphtalene carboxylic acids, amino anthracene carboxylic acids as well as their sulfonic acid counterparts, aminopyrimidine carboxylic acids and their crosslinkable and potentially crosslinkable derivatives. Crosslinkable or potentially crosslinkable moieties are selected from a group comprising amino-, nitro-, cyano-, halogene, acetylene, vinyl, acrylic moieties. Crosslinking can be achieved after linear polymers of high molecular weight are produced from low molecular weight prepolymers. Depending upon the crosslinkable groups(s) available on the amino acids, multifunctional epoxides, isocyanates, quinones, anhydrides, aziridines, titanates, zirconyl salts, preformed epoxy-or phenolic resins, radical or ionic polymerization catalysts can be used for curing. Polymers can be prepared either from a single amino acid or a combination of different amino acids to obtain polymers with varying characteristics.

1 Claim, 1 Drawing Sheet

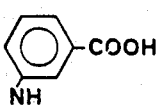
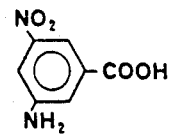
A₁       A'₁
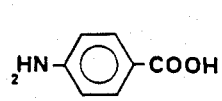
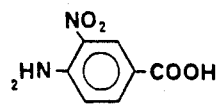
A₂       A'₂
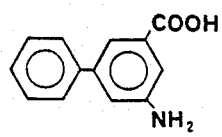 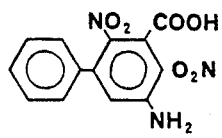 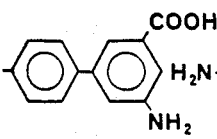
B₁    B'₁    B''₁    B'''₁
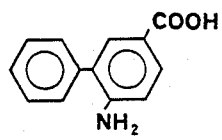 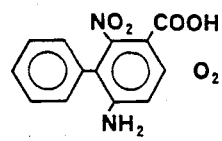 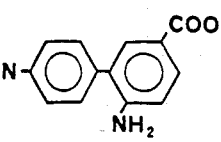
B₂    B'₂    B''₂    B'''₂
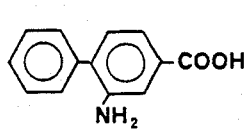 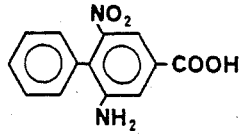
B₃       B'₃
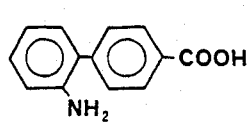 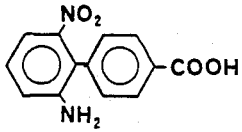
B₄       B'₄
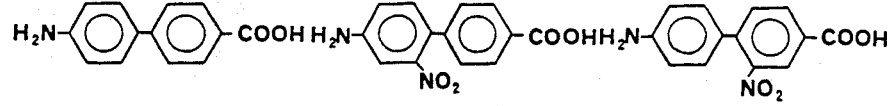
B₅       B'₅       B''₅

CROSSLINKABLE ARAMIDS

BACKGROUND OF THE INVENTION

1. Field of the Invention

This invention relates to the development of a class of polymers that have not been described before, utilizing several classes of artificial amino acids and their crosslinkable or potentially crosslinkable derivatives. Since many of these amino acids have not been conceived for aramid production, the invention also relates to the uncrosslinked polymers formed from them.

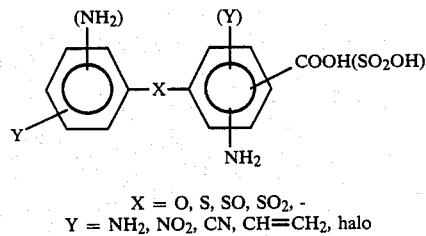

X = O, S, SO, SO$_2$, -
Y = NH$_2$, NO$_2$, CN, CH=CH$_2$, halo

2. Description of Prior Art

Fully aromatic polyamide was first developed in 1966 by DuPont from m-phenylene diamine and isophthalic acid dichloride and was named "Nomex". This was followed, in quick succession by "Conex" in Japan and "Fenilon" in Russia. In 1972 DuPont introduced "Kevlar", produced from p-phenylenediamine and terephthalic acid dichloride. Because of the insolubility of the polymer in organic solvents its development took a long time and while other aramids could be spun into fibers directly from the solution in which they were formed, "Kevlar" required dissolution in concentrated sulfuric acid for spinning. To obtain polymers that were easier to manipulate, mixtures of the amines and the acid chlorides have also been used, due to the increased solubility of such mixtures. Formation of fibers require very high molecular weight polymers. Several methods were developed to obtain such polymers which include:

1. Interfacial polycondensation.
2. Low temperatures solution polycondensation.
3. Direct polycondensation of the acid and amine in the presence of activating chemicals such as phosphites.

Since the first of these yielded only low to moderate molecular weight polymers, most aramids were developed using the latter two methods.

SUMMARY OF THE INVENTION

This invention relates generally to a class of polymers utilizing several classes of artificial aromatic amino acids and their crosslinkable or potentially crosslinkable derivatives as set forth in FIG. 1.

Since there are 24 different amino acids that can be formed with three different substituents on a single ring of a diphenylmolecule; for the sake of simplicity and to save space only a few select examples of the amino acid precursors are going to be given in FIG. 2, based on the diphenyl nucleus. The amino acids based on diphenyl ether-, diphenylsulfide-, etc.-nucleus are similar but not necessary limited to the isomers given.

Similarly, for the sake of simplicity only the potentially crosslinkable nitro derivatives are shown in FIG. 1 and the examples that follow under the preferred embodiments, even though other moieties can easily be substituted for the nitro group, in order to achieve different characteristics of the final product. The process briefly consists of the following steps:

I. Polymerization of the amino acids
II. Curing of the polymer

I. Polymerization of the amino acids can be performed to yield:
1. Low molecular weight polymers
2. High molecular weight polymers
To achieve these
   a. Interfacial polycondensation,
   b. Low temperature solution polycondensation,
   c. Polycondensation in the presence of activating compounds have been used.

II. Curing can be performed.
1. Either on the polymer, in bulk, or
2. After fibers films etc. are shaped, woven etc. into their final form.

DESCRIPTION OF THE PREFERRED EMBODIMENTS OF THE INVENTION

I. Interfacial polycondensation:

a. High molecular weight (HMW) form:

An emulsion is prepared of 8.48 g sodium carbonate, 0.2 g sodium dodecyl sulfate, 25 ml tetrahydrofuran (THF) in 75 ml of water with rapid stirring. Into this emulsion is added 9.75 g 3-amino 5-nitro benzoylchloride hydrochloride in 17 ml benzonitrile and 9 ml THF. Stirring is continued for 10 minutes. The mixture is poured into hot water and the precipitated polymer is washed with water and methanol and dried in a vacuum oven.

b. Low Molecular Weight (LMW) form:

To ensure LMW form in the above procedure solvents were mixed with form 0.1 to 1% of primary amines, such as ethylamine aniline and phenylisocyanate.

II. Low temperature solution polycondensation:

a. HMW form:

A 500 ml three necked flask was dried in an oven at 160° C. for two hours and was placed in a dry box. 52 ml hexamethylphosphoramide, distilled from calcium hydride at reduced pressure and stored over calcium hydride, was filled into an Erlenmeyer flask in the dry box, sealed and cooled on ice. 7.5 ml (THF), distilled and stored over metallic sodium, was placed in an Erlenmeyer flask, sealed and cooled on ice. 14.3 g (65 m mole) of 4-amino 3 nitro benzoylchloride hydrochloride was weighed in the dry box and placed in a reaction flask, which was connected with a stirrer, nitrogen inlet tube and calcium chloride drying tube and cooled in an ice bath. Just before polymerization, 0.12 ml benzoylchloride was added to the THF and the mixture was added to the reaction flask with moderate stirring for one minute. The stirring rate was increased and hexamethylphosphoramide added rapidly. The mixture, which rapidly gels, was stirred for one hour while being cooled in the ice bath. The bath was then removed and the polymer mass was allowed to stand overnight at room temperature.

The solid gel was combined with water in a blender at high speed where it was converted into a fine white powder. It was washed three times with water and once with ethanol in the blender, being filtered on medium pore Buchner funnel and dried in a vacuum oven overnight at 80°–90° C. (46,47).

b. LMW form:

1. Time study:

The reaction as under (a) was performed in a flask that also has a tube to draw samples. After the reaction mixture was completed by the addition of hexamthyl phosphoramid, samples were taken first every two minutes and after 10 minutes every 10 minutes. The polymers in the samples were treated as above. Reaction products obtained within 2–20 minutes were found to be satisfactory.

2. Use of chain terminators:

To a polymerization mixture containing 200 ml tetramethylurea, which is cooled in ice bath, 2.5 m moles of designated terminator-aniline, ethylamine, phenylisocyanate—and 32 g (17 m mole) of p-aminobenzoylchloride hydrochloride were added. The contents were stirred for 15 minutes after which the cooling bath was removed and the contents were stirred for 105 minutes. Then 12.8 g (31 m mole) lithium hydroxide was added and the contents were stirred for another 60 minutes after which the mixture was allowed to stand for 20 hours at ambient temperature. The mixture was mixed in a blender with water to precipitate the polymer, which was collected, washed three times with water and once, with alcohol and dried in a vacuum oven.

III. Polycondensation in the presence of activating compounds:

A. Polycondensation in the presence of phosphites.

a. HMW form:

To a stirred solution of 6.0 g (63 m mole) of phenol in 10 ml of pyridine under nitrogen and cooled to 0° C. was added 1.75 ml (20 m mole) phosphorous trichloride. The mixture was stirred for one hour at room temperature under nitrogen and 5.9 g (20 m mole) 3-amino-5-nitrodiphenyl carboxylic acid, 2 g (4%) of lithium chloride and 40 ml of dry N-methylpyrrolidone were added with stirring. The mixture was heated, gradually, at 80°–90° C. for two hours and at 100°–105° C. for four hours, with continuous stirring under nitrogen. The mixture was allowed to cool to 60°–80° C. and poured into 300 ml of methanol with vigorous stirring. Fibrous white polymer was collected with filtration and washed four times with methanol and dried in a vacuum oven at 100° C. (9).

b. LMW form:

1. Time study:

A time study, as detailed above, was performed to be able to establish a correlation between the molecular size and time. Products from a reaction period of 2–20 minutes were found to be satisfactory.

2. Use of chain terminators:

As discussed above, inclusion of monofunctional reactive moieties was found to produce satisfactory products.

B. Polycondensation in the presence of triphenyl phospine:

a. HMW form:

0.1 mole of 4'-amino-3-nitrodiphenyl carboxylic acid and triphenyl phosphine are dissolved in 100 ml pyridine and 0.1 mole of hexachloroethane was added to the solution with stirring at room temperature. An exothermic reaction takes place as soon as the polyhalo compound was added and the solution became turbid and entire solution solidified in 5 minutes. Excess acetone was added to remove solvent and byproducts from the polymer which was isolated by filtration. The polymer was washed repeatedly with water and acetone and dried under reduced pressure.

b. LMW form:

0.1 mole of 3-aminodiphenyl carboxylic acid and triphenyl phosphine were dissolved in 100 ml pyridine and 0.1 mole of carbon tetrabromide was added and the product was isolated as described above. The same experiment was repeated with different perhalo compounds such as perhaloacetone, isopropyltrichloro acetate, using varying ratios of monomers to perhalo compounds.

Reduction of nitro groups:

There are several classical methods for the reduction of nitro groups used in organic chemistry. What is unique here is the application of these methods to a polymer where nearly all of these groups have to be reduced to attain optimal crosslinking density, on the one hand, and to eliminate any complications that may arise, during HTP, due to the presence of strongly oxidizing groups, on the other. The problem is more serious with HMW form of the polymer due to its decreased solubility. The literature, however, provides us with many solvents and solvent adducts that increase solubility, such as inorganic salts like lithium chloride or organic compounds like tetramethyl urea. With LMW forms, solubility is not a problem and reduction can occur smoothly.

The polymers were dissolved in appropriate solvents and treated with the following chemicals:

metallic tin + hydrochloric acid metallic zinc + hydrochloric acid stannous chloride + hydrochloric acid as well as catalytic hydrogenation, according to established procedures.

In each case the present of any remaining nitro groups were tested first qualitatively, using spot tests and after acid hydrolysis of the samples.

For the qualitative test the methods of F. Feigl; Feigl, Anger and Frehden and of Bose were used.

After acid hydrolysis and the removal of the acid, the sample was subjected to thin layer chromatography against standards.

If any unreduced nitro groups were detected, the polymers were subjected to a second cycle of reduction and tested again for the unreduced nitro groups.

Curing

Different crosslinking agents were used:

1. Polyfunctional epoxides, divinylbenzenedioxide, diglycidylether of resorcinol,
2. Pyromellitic acid dianhydride, methylnadic anhydride
3. Polyfunctional isocyanates,
4. p-benzoquinone.

1. This is the reverse reaction of epoxy resin curing. The polymers were dissolved in an appropriate solvent after estimating the available amino content and the stoichimetric amount of the epoxides were added, and the mixture was thoroughly mixed and curing followed at ambient temperature as well as at elevated temperatures according to established procedures. The latter epoxide can be expected to provide a little less brittle material.

2. These reactions provide very brittle cured material with excellent high temperature characteristics. The polymers and pyromellic acid dianhydride were dissolved in a solvent and curing was effected at elevated temperatures, 120°–200° C.

3. For applications that do not require exposure to high temperatures while requiring excellent moisture resistance, use of isocyanates for curing enables one to effect cure at low temperature.

4. This is a reaction we have extensive experience in and takes advantage of the spontaneous reaction between quinones and amines. The interesting feature here is that when crosslinking is accomplished, one gets a phenolic group as the bridge, which contributes to high temperature performance. The polymers and p-benzoquinones are dissolved in an appropriate solvent at a ratio of 1:2 and curing effected by heating.

What is claimed is:

1. The amino acid which is

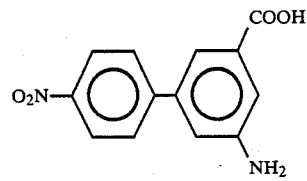

* * * * *